United States Patent [19]

Giolito et al.

[11] Patent Number: 4,559,184

[45] Date of Patent: Dec. 17, 1985

[54] PHOSPHATE ESTER SYNTHESIS WITHOUT PHOSPHORYLATION CATALYST

[75] Inventors: Silvio L. Giolito, Whitestone, N.Y.; Stanley B. Mirviss, Stamford, Conn.

[73] Assignee: Stauffer Chemical Company, Westport, Conn.

[21] Appl. No.: 551,641

[22] Filed: Nov. 14, 1983

[51] Int. Cl.$^4$ .............................................. C07F 9/09
[52] U.S. Cl. ................................................ 260/974
[58] Field of Search ...................................... 260/974

[56] References Cited

U.S. PATENT DOCUMENTS

| | | | |
|---|---|---|---|
| 1,425,392 | 8/1922 | Laska et al. | 260/974 |
| 1,958,210 | 5/1934 | Scott | 260/974 |
| 2,078,421 | 4/1937 | Shuman | 260/974 |
| 2,168,587 | 8/1939 | Shuman | 260/974 |
| 4,139,487 | 2/1979 | Garrett | 260/974 |
| 4,351,780 | 9/1982 | Giolito et al. | 260/974 |

Primary Examiner—Anton H. Sutto
Attorney, Agent, or Firm—Roger S. Benjamin

[57] ABSTRACT

Triarylphosphates are prepared by phosphorylation of alkylphenols without use of phosphorylation catalyst. An improved phosphorylation step includes preheating alkylphenol feedstock to 150° C. and completing reaction at 215° C. or above in the presence of a stoichiometric excess of alkylphenol. The absence of phosphorylation catalyst simplifies distillative purification of reaction product by eliminating the need to withdraw purified product as distillate.

10 Claims, No Drawings

PHOSPHATE ESTER SYNTHESIS WITHOUT PHOSPHORYLATION CATALYST

BACKGROUND OF THE INVENTION

Triarylphosphates have established utility as functional fluids because of their plasticizer and lubricant properties. Particularly useful are "synthetic" triaryl phosphates prepared from mixtures of phenol and alkylphenols wherein the alkyl group contains 3 or 4 carbon atoms. Thus, triaryl phosphates such as isopropylphenyl/phenyl/phosphates and tertiarybutylphenyl/phenyl phosphates are prepared to have desirable properties of low color, viscosity, pour point, etc.

Conventional processes for forming triaryl phosphates employ two steps. The first step is alkylation of phenol with an olefin to give an alkylphenol feedstock. The second step employs heat and catalyst to phosphorylate the feedstock and yield a crude phosphate ester product. Depending on the intended use of the triarylphosphate, a third process step may be used to purify the crude product by distillation. Typical triarylphosphate synthesis and purification steps are described in U.S. Pat. Nos. Re. 29,540 and 4,139,487.

The prior art describes triaryl phosphate synthesis absent phosphorylation catalyst. For example, U.S. Pat. Nos. 1,425,392; 2,078,421; and 2,168,587 phosphorylate cresols, tertiary amyl phenols, and petroleum phenols at elevated temperatures.

The use of catalysts such as $MgCl_2$ or $AlCl_3$ in the phosphorylation step generally enhances reaction rate but subsequent removal of the catalyst is required in a purification step.

It is desirable to develop improved phosphorylation techniques for preparing triarylphosphates which will permit simpler and less costly purification.

FIELD OF THE INVENTION

This invention is an improved process for making triarylphosphates from the phosphorylation of alkylphenols.

SUMMARY OF THE INVENTION

The process of this invention uses a phosphorylation having the essential steps of (a) preheating the alkylphenol feedstock, (b) combining a stoichiometric excess alkylated phenol feedstock with phosphorylation agent, (c) heating the reaction mixture to a selected temperature until reaction is complete, and (d) operating steps (b), and (c) in the absence of phosphorylation catalyst. An additional embodiment of the invention is purification of the reaction product by distillation without removing desired final product as a vapor phase condensed distillate.

DETAILED DESCRIPTION OF THE INVENTION

The phosphate esters produced by the process of this invention are mixtures of one or more triarylphosphates represented by the formula, $(RO)_3PO$ wherein the R groups are the same or different and are selected from phenyl or alkylphenyl, said alkylphenyl having an alkyl moiety of three or four carbon atoms, with the proviso that said triarylphosphates have an average mole ratio of alkyl moiety to phenyl group of from about 0.1:1 to about 0.75:1.

Particularly preferred phosphate esters are isopropylphenyl/phenyl phosphates, secondary butylphenyl/phenyl phosphates, and tertiary butylphenyl/phenyl phosphates.

The process of this invention is an improvement over the conventional triarylphosphate forming process using the sequential steps of alkylation and phosphorylation. An additional process step in conventional triarylphosphate forming processes is purification of the crude phosphate ester reaction product by distillation and/or washing.

The details of conventional alkylation, phosphorylation, and purification processes for forming triarylphosphates are described in U.S. Pat. Nos. 3,576,923 and 4,139,487; the disclosures of which are incorporated herein by reference.

The process of the invention is practiced by making the following changes in the conventional phosphate ester forming process.

THE FIRST STEP ALKYLATION

The alkylation step for the process is the same as the conventional alkylation procedure except that any catalyst chosen to assist the alkylation should either be of a kind or an amount ineffective as a phosphorylation catalyst. It can be of a type that is readily removed because of its insoluble nature (e.g., an acidic clay). Any catalyst present in the alkylate which would be effective for promoting phosphorylation should be removed or inactivated before transferring the alkylphenol feedstock to the phosphorylation step of the process.

The term "alkylphenol feedstock" as used herein is defined to be a mixture of unreacted phenol, monoalkylated phenols, and minor portions of polyalkylated phenols, or fractionated portions of this mixture. The alkylphenol feedstock is limited to products of phenol alkylated with olefins having three or four carbon atoms. Illustrative olefins useful for effecting alkylation are propene, isobutylene, or diisobutylene.

THE SECOND STEP PHOSPHORYLATION

The phosphorylation step is carried out by contacting the alkylphenol feedstock of the first process step with phosphorylating agent. Typical phosphorylating agents are phosphorus oxychloride, phosphorus oxybromide, or phosphoric acid. Phosphorus oxychloride is the preferred phosphorylating agent.

The phosphorylation step is modified by the following conditions to conform it to the process of the invention:

(a) the alkylated phenol feedstock from the first process step is heated to at least 150° C. before contact with the phosphorylating agent.

(b) the alkylated phenol feedstock of step (a) is combined with phosphorylating agent in such proportions that the feedstock is in stoichiometric excess. Generally, it is desired that the alkylated phenol feedstock be used in at least five weight percent excess of its stoichiometric requirements (based on the weight of alkylated phenol).

(c) the reaction mixture of step (b) containing alkylated phenol and phosphorylating agent is heated to a temperature of at least 215° C. This temperature level is maintained until the phosphorylation reaction is essentially complete. It is preferred to heat the reaction mixture in this step to about at least 245° C. It is also recommended that the heating rate of this step of the reaction be performed as rapidly as practical operation allows.

The completion of the reaction in this phosphorylation step may be determined by monitoring the evolution of HCl gas from the reaction zone. Alternatively, aliquot portions of the reaction mixture may be withdrawn for analysis.

It is a discovery of this invention that by conducting the phosphorylation reaction under the changed reaction conditions of this invention, the phosphorylation reaction proceeds at nearly the same rate and with nearly the same yield of triaryl phosphate as when phosphorylation is carried out with a conventional catalyzed reaction.

The attendant advantage of operating by the process of this invention is that the crude triaryl phosphate reaction product from the second step has no phosphorylation catalyst (especially, nonvolatile salts) to be removed.

PURIFICATION STEP

The process of this invention may be practiced solely by operation of the first and second process steps in the manner described. Generally, however, the crude reaction product of the second step must be further processed to have utility as a functional fluid.

The essential process of the purification step is distillation. Moreover, the distillation is performed in two distinct phases.

Initially the crude phosphate ester reaction product should be distilled to remove unreacted phenol and alkylphenols from the stoichiometric excess of feedstock.

The second phase of the distillation is initiated when the unreacted phenolics have been essentially removed from the crude phosphate ester reaction product. Thereafter, the reaction product is fractionated by removing portions of lower boiling phosphate ester as distillate. The removal of lower boiling phosphate esters is continued until the distillation residue has the chemical and physical characteristics (e.g., viscosity, alkyl/phenol ratio) desired in the phosphate ester product. Generally the distillation of phosphate ester is conducted at subatmospheric pressure (preferably less than 10 millimeters of Hg) to avoid phosphate ester decomposition.

An important advantage of the above-described purification process is that the triarylphosphate does not have to be vaporized and removed in that phase from the distillation zone to be recovered as a condensed distillate product. The triarylphosphate product of this invention may be recovered as a liquid in the form of a distillation residue. Moreover, the absence of a catalyst salt avoids a distillation residue recovery/disposal problem.

The purification process may be supplemented by conventional washing or other purification procedures if desired.

The process of the invention may be better understood by reference to the following Examples.

EXAMPLE I

Apparatus

A 500 ml. flask was equipped with a thermometer, stirring rod, and reflux condenser. One neck of the flask held a dropping funnel for addition of $POCl_3$. The flask and contents were heated with a thermostatically controlled heating mantle. HCl gas expelled from the flask was collected in a trap containing caustic solution.

General Procedure

One mole of mixed isopropyl phenols/phenol feedstock was reacted with 0.33 moles of $POCl_3$. The flask contents were stirred continuously to assist HCl removal from the reaction mixture. When HCl production stopped, the reactor was cooled below 90° C. and the reaction product sparged with nitrogen.

Sample A

Isopropylphenyl/phenyl phosphate was prepared by charging $POCl_3$ to the flask at room temperature and slowly heating the charge to 255° C. over a 12 hour period. The gradual progress of the reaction is shown in Table I.

Sample B

This control experiment was run in a manner similar to Sample A but using 1 weight percent (based on isopropylphenol) of $MgCl_2$ phosphorylation catalyst. The heating rate was faster than for Sample A but Table I confirms that the rate of reaction was significantly faster.

Sample C

This experiment employed preheating of the alkylphenol before addition of the phosphorylation agent. The alkylphenol was heated to 165° C. prior to addition of the $POCl_3$. After the $POCl_3$ was added, the mixture was rapidly heated to 295° C. This method resulted in an increased rate of reaction in the initial stage, but did not change the required reaction time. The reaction rate is displayed in Table I.

Sample D

This sample represents the practice of the invention. A 5 weight percent excess of isopropylphenol was heated to 150° C. and $POCl_3$ slowly added while rapidly heating the mixture to 245° C. This procedure resulted in a faster reaction and 95% yield of desired product (based on HCl) evolved.

Sample E

This experiment is outside the practice of the invention and is a comparison to the practice of Sample D.

Five weight percent excess isopropylphenol was used. The isopropylphenol was initially heated to 100° C. and slowly heated thereafter to 197° C. with $POCl_3$ addition. The slower reaction rate is shown by the numbers in Table I.

TABLE I

| Sample | Reaction Time Minutes | Percent Completion of Reaction |
|---|---|---|
| A | 100 | 30 |
| A | 150 | 35 |
| A | 200 | 42 |
| A | 250 | 52 |
| A | 300 | 58 |
| A | 325 | 60 |
| A | 450 | 80 |
| A | 475 | 81 |
| A | 725 | 88 |
| B | 50 | 91 |
| B | 100 | 97 |
| B | 140 | 99 |
| C | 50 | 25 |
| C | 100 | 48 |
| C | 150 | 64 |
| C | 200 | 73 |
| C | 250 | 78 |

TABLE I-continued

| Sample | Reaction Time Minutes | Percent Completion of Reaction |
|---|---|---|
| C | 300 | 82 |
| C | 400 | 83 |
| C | 450 | 88 |
| C | 580 | 90 |
| C | 725 | 92 |
| D | 50 | 83 |
| D | 75 | 90 |
| D | 175 | 95 |
| E | 100 | 7 |
| E | 160 | 12 |
| E | 200 | 17 |
| E | 260 | 29 |
| E | 290 | 42 |
| E | 340 | 60 |
| E | 400 | 68 |
| E | 430 | 72 |
| E | 630 | 86 |

EXAMPLE II

Sample F

The experiment of this Example employs the same apparatus as Example 1. A sample of mixed tertiarybutylphenols having a $C_4$ to phenol ratio of 0.3 was heated to 160° C. and reacted in 5 weight percent stoichiometric excess with $POCl_3$. The temperature was raised to 216° C. as rapidly as possible. No catalyst was employed.

A 99% yield of desired product was obtained in three hours by following the practice of the invention. The reaction rate is displayed in Table II.

Sample G

This Example is a control experiment using a catalyst and forms a comparison to Sample F. The procedure of Example F was used except that $MgCl_2$ catalyst was added. The reaction rate is shown in Table II.

The reaction rates and yields of Sample F and Sample G are comparable.

TABLE II

| Sample | Reaction Time Minutes | Percent Completion of Reaction |
|---|---|---|
| F | 20 | 23 |
| F | 40 | 47 |
| F | 60 | 53 |
| F | 80 | 61 |
| F | 100 | 69 |
| F | 120 | 77 |
| F | 140 | 90 |
| F | 160 | 90 |
| F | 180 | 99 |
| G | 20 | 32 |
| G | 40 | 42 |
| G | 60 | 53 |
| G | 80 | 68 |
| G | 100 | 75 |
| G | 120 | 81 |
| G | 140 | 84 |
| G | 160 | 91 |
| G | 180 | 100 |

While this invention has been described with respect to certain embodiments, it is not so limited, and it is to be understood that variations and modifications may be made without departing from its scope.

The embodiments of the invention which are claimed are defined as follows.

We claim:

1. A process for preparing triaryl phosphates represented by the formula, $(RO)_3PO$ wherein the R groups are the same or different and are selected from phenyl or alkylphenyl, said alkylphenyl having an alkyl moiety of 3 or 4 carbon atoms, with the proviso that said triarylphosphates have an average mole ratio of alkyl moiety to phenyl group of from about 0.1:1 to about 0.75:1; which process comprises alkylating phenol in a first step to yield an alkylated phenol feedstock, then phosphorylating said phenol feedstock in a second step, wherein the improvement comprises:
   (a) heating the alkylated phenol feedstock from the first step to at least 150° C. before contact with phosphorylating agent, with the proviso that any catalyst chosen to assist the alkylation should be either of a kind or amount ineffective as a phosphorylation catalyst,
   (b) combining the alkylated phenol feedstock of step (a) with phosphorylating agent in such proportion that the feedstock is in stoichiometric excess,
   (c) heating the mixture of alkylated phenol feedstock and phosphorylating agent to a temperature of at least 215° C. until the phosphorylation reaction is essentially completed; and
   (d) conducting steps (b) and (c) in the absence of an effective amount of phosphorylation catalyst.

2. The process of claim 1 wherein the triaryl phosphates are selected from the group consisting of isopropylphenyl/phenyl phosphates, or tertiarybutylphenyl/phenyl phosphates.

3. The process of claim 1 wherein the stoichiometric excess of alkylated phenol feedstock in step (b) is about at least 5 weight percent excess based on the weight of said feedstock.

4. The process of claim 1 wherein the mixture of step (c) is heated to a temperature of about at least 245° C.

5. A process for preparing triaryl phosphates represented by the formula, $(RO)_3PO$ wherein the R groups are the same or different and are selected from phenyl or alkylphenyl, said alkylphenyl having an alkyl moiety of 3 or 4 carbon atoms, with the proviso that said triaryl phosphates have an average value mole ratio of alkyl moiety to phenyl group of from about 0.1:1 to about 0.75:1; which process comprises alkylating phenol in a first step to yield an alkylated phenol feedstock, phosphorylating said phenol feedstock in a second step, and purifying the second step phosphate ester by distillation in a third process step, wherein the improvement comprises:
   (a) heating the alkylated phenol feedstock from the first step to at least 150° C. before contact with phosphorylating agent, with the proviso that any catalyst chosen to assist the alkylation should be either of a kind or amount ineffective as a phosphorylation catalyst,
   (b) combining the alkylated phenol feedstock of step (a) with phosphorylating agent in such proportion that the feedstock is in stoichiometric excess,
   (c) heating the mixture of alkylated phenol feedstock and phosphorylating agent to a temperature of at least 215° C. until the phosphorylation reaction is essentially completed,
   (d) conducting steps (b) and (c) in the absence of an effective amount of phosphorylation catalyst,
   (e) distilling the product of step (c) to remove unreacted alkylphenol feedstock, and
   (f) distilling the product of step (e) at subatmospheric pressure and above ambient temperature to yield a distillation residue of liquid triaryl phosphate product.

6. The process of claim 5 wherein the triaryl phosphates are selected from the group consisting of isopropylphenyl/phenyl phosphates, secondary butylphenyl/phenyl phosphates, or tertiary butylphenyl/phenyl phosphates.

7. The process of claim 5 wherein the stoichiometric excess of alkylated phenol feedstock in step (b) is about at least 5 weight percent excess based on the weight of said feedstock.

8. The process of claim 5 wherein the mixture of step (c) is heated to a temperature of about at least 245° C.

9. The process of claim 5 wherein the distillation of step (f) is conducted at a pressure less than 10 millimeters of mercury absolute and a temperature in excess of 150° C.

10. The process of claim 5 wherein the distillation residue of step (f) is withdrawn as liquid from the distillation zone and further treated by washing.

* * * * *